United States Patent
Sugano et al.

(10) Patent No.: US 9,630,884 B2
(45) Date of Patent: Apr. 25, 2017

(54) COLORING AGENT COMPOSITION AND METHOD FOR PRODUCING SAME

(71) Applicant: YOSHINO GYPSUM Co., Ltd., Tokyo (JP)

(72) Inventors: Kenichi Sugano, Tokyo (JP); Masato Yoshikane, Tokyo (JP); Emi Mamada, Tokyo (JP)

(73) Assignee: YOSHINO GYPSUM CO., LTD., Tokyo (JP)

( * ) Notice: Subject to any disclaimer, the term of this patent is extended or adjusted under 35 U.S.C. 154(b) by 0 days.

(21) Appl. No.: 14/912,220

(22) PCT Filed: Sep. 18, 2014

(86) PCT No.: PCT/JP2014/074622
§ 371 (c)(1),
(2) Date: Feb. 16, 2016

(87) PCT Pub. No.: WO2015/045994
PCT Pub. Date: Apr. 2, 2015

(65) Prior Publication Data
US 2016/0200633 A1    Jul. 14, 2016

(30) Foreign Application Priority Data
Sep. 30, 2013    (JP) ................ 2013-203127

(51) Int. Cl.
| | | |
|---|---|---|
| C04B 40/00 | (2006.01) | |
| A61C 13/34 | (2006.01) | |
| C04B 28/14 | (2006.01) | |
| C04B 111/82 | (2006.01) | |

(52) U.S. Cl.
CPC .......... *C04B 40/0042* (2013.01); *A61C 13/34* (2013.01); *C04B 28/14* (2013.01); *C04B 40/0039* (2013.01); *C04B 2111/82* (2013.01); *Y02W 30/94* (2015.05)

(58) Field of Classification Search
CPC ..... A61C 13/34; C04B 18/146; C04B 20/008; C04B 22/143; C04B 28/14; C04B 40/0039; C04B 40/0042; C04B 2103/54; C04B 2111/82
See application file for complete search history.

(56) References Cited

U.S. PATENT DOCUMENTS

2010/0154680 A1    6/2010    Friedrich et al.

FOREIGN PATENT DOCUMENTS

| | | | |
|---|---|---|---|
| CN | 101665631 | | 3/2010 |
| CN | 102765924 | | 11/2012 |
| JP | 63139039 | | 6/1988 |
| JP | 63205370 | | 8/1988 |
| JP | 0912422 | | 1/1997 |
| JP | 1060302 | | 3/1998 |
| JP | 2011121924 | | 6/2011 |
| KR | 1020090041857 A | * | 4/2009 |
| KR | 10-2010-0002241 | * | 1/2010 |
| KR | 10-2010-0002241 A | * | 1/2010 |
| SU | 712427 | * | 1/1980 |

OTHER PUBLICATIONS

International Search Report issued in the corresponding International PCT application No. PCT/JP2014/074622, dated Dec. 16, 2014, 4 pages.

Chinese Office Action, issued in the corresponding Chinese patent application No. 201480038725.8 dated Nov. 17, 2016, 7 pages.

\* cited by examiner

*Primary Examiner* — Anthony J Green

(74) *Attorney, Agent, or Firm* — Hamre, Schumann, Mueller & Larson, P.C.

(57) ABSTRACT

Provided is a coloring agent composition to be added to a gypsum-containing raw material powder constituting a gypsum product and to be used for coloring the gypsum product, the coloring agent composition being a powder containing a pigment, calcined gypsum, and amorphous silica. A process for producing the coloring agent composition includes a first step of mixing a pigment, calcined gypsum, and amorphous silica to obtain a mixed powder. Use of the coloring agent composition makes it possible to easily produce gypsum products such as a powder and a hardened body that are excellent in colorability.

12 Claims, No Drawings

COLORING AGENT COMPOSITION AND METHOD FOR PRODUCING SAME

TECHNICAL FIELD

The present invention relates to a coloring agent composition to be used for coloring a gypsum product and a process for producing the coloring agent composition.

BACKGROUND ART

Gypsum products such as a dental model, an industrial model, and a wall-plastering material are sometimes appropriately colored according to their application. For example, the dental model (teeth model) can be prepared by pouring gypsum that is mixed with water into a female impression of teeth formed from a plastic material or the like to cure the gypsum, and then removing the impression of teeth (see, for example, Patent Literature 1 and Patent Literature 2). In preparing the dental model, a pigment is added to a powder of gypsum as a raw material to color the dental model to be obtained into a desired color.

In order to improve the colorability of a gypsum product to be obtained, such as a dental model, it usually becomes necessary to increase the amount of the pigment added to the gypsum. However, when the addition amount of the pigment is increased, it sometimes occurs that the cost required for coloration increases and the strength of the gypsum product to be obtained, which is a hardened body, is lowered.

Moreover, in the case where, for example, a colored gypsum hardened body such as a dental model is produced, gypsum that is mixed with water, when poured into an impression of teeth, is given mechanical vibration using a vibrator or the like. Thereby, the fluidity of the gypsum is secured and bubbles inside are removed. However, there has been a problem that, when the mechanical vibration is given to the gypsum that is mixed with water, the pigments aggregate to make color unevenness liable to occur in the gypsum hardened body to be obtained.

CITATION LIST

Patent Literature

Patent Literature 1: Japanese Patent Laid-Open No. 9-12422
Patent Literature 2: Japanese Patent Laid-Open No. 2011-121924

SUMMARY OF INVENTION

Technical Problem

In order to solve the above-described problem, a method is sometimes adopted in which a diluted pigment obtained by diluting a pigment with a base material such as, for example, calcined gypsum or calcium carbonate is prepared as a coloring agent (master batch) in advance and the diluted pigment is then added to a powder of gypsum as a raw material to color a gypsum product. However, even when such a method is adopted, the extent of coloration is insufficient in some cases.

The present invention has been made in consideration of such problems of conventional technologies, and the subject of the present invention is to provide a coloring agent composition that can easily produce a gypsum product, such as a powder and a hardened body, that is excellent in colorability and a process for producing the gypsum product.

Solution to Problem

The present inventors have made diligent studies to achieve the subject to find that the above-described subject can be achieved by blending a pigment, calcined gypsum, and amorphous silica, and have completed the present invention.

That is to say, the following coloring agent composition is provided according to the present invention.

[1] A coloring agent composition to be added to a gypsum-containing raw material powder constituting a gypsum product and to be used for coloring the gypsum product, the coloring agent composition being a powder containing: a pigment; calcined gypsum; and amorphous silica.

[2] The coloring agent composition according to [1], wherein the amorphous silica has a number average particle diameter of 5 to 40 nm.

[3] The coloring agent composition according to [1] or [2], wherein a content of the amorphous silica is 0.01 to 1 part by mass relative to 1 part by mass of the pigment.

[4] The coloring agent composition according to any one of [1] to [3], wherein a content of the calcined gypsum is 1 to 100 parts by mass relative to 1 part by mass of the pigment.

[5] The coloring agent composition according to any one of [1] to [4], wherein the calcined gypsum is at least one selected from the group consisting of α hemihydrate gypsum, hemihydrate gypsum, and type III anhydrous gypsum.

Moreover, the following process for producing a coloring agent composition is provided according to the present invention.

[6] A process for producing the coloring agent composition according to any one of [1] to [5], the process including a first step of mixing the pigment, the calcined gypsum, and the amorphous silica to obtain a mixed powder.

[7] The process for producing the coloring agent composition according to [6], wherein the pigment, the calcined gypsum, and the amorphous silica are pulverized concurrently with being mixed in the first step.

[8] The process for producing the coloring agent composition according to [6], further including a second step of pulverizing the mixed powder.

[9] The process for producing the coloring agent composition according to any one of [6] to [8], wherein the calcined gypsum has a volume average particle diameter of 20 to 200 μm.

Advantageous Effects of Invention

The coloring agent composition according to the present invention makes it possible to easily produce a gypsum product, such as a powder and a hardened body, which is excellent in colorability. Moreover, the process for producing a coloring agent composition according to the present invention makes it possible to produce the coloring agent composition with the above-described properties.

Furthermore, a gypsum hardened body (colored gypsum hardened body) prepared using the coloring agent composition according to the present invention has not only an improved colorability but also an improved color unevenness.

DESCRIPTION OF EMBODIMENTS

Hereinafter, the embodiments according to the present invention will be described, however the present invention is not limited to the following embodiments.

<Coloring Agent Composition>

The coloring agent composition according to the present invention is a powder containing a pigment, calcined gypsum, and amorphous silica. And the coloring agent composition according to the present invention is added to a raw material powder containing gypsum that constitutes a gypsum product (matter to be colored), and is used as a coloring agent (so-called master batch) for coloring the gypsum product.

(Pigment)

The kind of a pigment to be used is not particularly limited, and pigments generally used for coloring industrial products and the like can be used. Specific examples of the pigment that can be used include: organic pigments such as azo pigments and polycyclic pigments; inorganic pigments such as natural mineral pigments and synthetic inorganic pigments; and so on.

(Calcined Gypsum)

The coloring agent composition according to the present invention contains calcined gypsum. The calcined gypsum is a powdered or particle component that can function as a base material. It is preferable that the content of the calcined gypsum in the coloring agent composition is 1 to 100 parts by mass relative to 1 part by mass of the pigment, more preferably 1 to 50 parts by mass. When the content of the calcined gypsum is less than 1 part by mass relative to 1 part by mass of the pigment, there is a tendency that colorability is difficult to improve and color unevenness is liable to occur in the colored gypsum hardened body to be obtained. Moreover, there is also a tendency that the kneading performance of the gypsum product (colored gypsum powder) with water gets worse in the case where the gypsum product is constituted from calcined gypsum. On the other hand, when the content of the calcined gypsum exceeds 100 parts by mass relative to 1 part by mass of the pigment, there is a tendency that the color unevenness is liable to occur in the colored gypsum hardened body.

Examples of the kind of calcined gypsum include a hemihydrate gypsum, β hemihydrate gypsum, and type III anhydrous gypsum. These kinds of calcined gypsum can be used alone or in combination of two or more.

(Amorphous Silica)

The coloring agent composition according to the present invention contains amorphous silica. By containing the amorphous silica, the coloring agent composition, when compared with the case where the amorphous silica is not contained, can be prepared so as to make the color unevenness difficult to occur in the colored gypsum hardened body and also make it possible to produce a gypsum product having a remarkably improved colorability. It is preferable that the content of the amorphous silica in the coloring agent composition is 0.01 to 1 part by mass relative to 1 part by mass of the pigment, more preferably 0.1 to 0.8 parts by mass. When the content of the amorphous silica is less than 0.01 parts by mass relative to 1 part by mass of the pigment, it becomes difficult to obtain effects due to blending of the amorphous silica. Thus, there is a tendency that the colorability of the gypsum product is difficult to improve and the color unevenness is liable to occur in the colored gypsum hardened body. On the other hand, when the content of the amorphous silica exceeds 1 part by mass relative to 1 part by mass of the pigment, there is a tendency that the effects hit the ceiling and disadvantage arises in terms of costs.

It is preferable that the amorphous silica has a number average particle diameter of 5 to 40 nm, more preferably 5 to 30 nm. The amorphous silica having a number average particle diameter of less than 5 nm is difficult to handle and is substantially difficult to prepare or obtain because the particle diameter is too small. On the other hand, when the amorphous silica has a number average particle diameter of more than 40 nm, there is a tendency that the colorability of the gypsum product is difficult to improve and the color unevenness is liable to occur in the colored gypsum hardened body. In addition, the "number average particle diameter of the amorphous silica" in the present DESCRIPTION means the "number average particle diameter of primary particles of the amorphous silica".

(Other Components)

Another component that is different from the above-mentioned respective components can be contained as necessary in the coloring agent composition according to the present invention. Examples of the another component that can be contained include, but not particularly limited to, additives that can generally be contained in gypsum products.

<Method of Using Coloring Agent Composition>

Use of the coloring agent composition according to the present invention makes it possible to easily produce a colored gypsum product. Hereinafter, an example of the method of using the coloring agent composition according to the present invention will be described taking the case where a dental model is produced as an example.

In order to produce a colored teeth model, a raw material powder which contains gypsum that constitutes the teeth model is prepared in the first place. As the gypsum, the calcined gypsum, such as α hemihydrate gypsum, β hemihydrate gypsum, and type III anhydrous gypsum, that constitutes a general teeth model can be used as it is.

Subsequently, the coloring agent composition according to the present invention is added to and mixed with the prepared raw material powder. The addition amount of the coloring agent composition may appropriately be set in consideration of the color, extent of coloration, cost, and so on of the teeth model intended to be produced. Specifically, the addition amount may be approximately 0.01 to 3 parts by mass relative to 100 parts by mass of the gypsum in the raw material powder. In addition, various additives including a hardening adjuster such as sodium citrate can be added to the raw material powder.

The method of mixing the raw material powder and the coloring agent composition is not particularly limited. Specifically, mixing can be performed by a simple method such as placing the raw material powder and the coloring agent composition into a container or bag and shaking the resultant mixture. That is to say, use of the coloring agent composition according to the present invention makes it possible to produce a gypsum product (colored gypsum powder) in which the color unevenness hardly occurs and which is excellent in colorability without using a special mixing apparatus or the like. A colored gypsum slurry can be obtained by adding an appropriate amount of mixing water and stirring the resultant mixture after mixing the raw material powder and the coloring agent composition. And a teeth model which is excellent in colorability, in which the color unevenness does not occur, and which is uniformly colored can be produced by pouring the obtained gypsum slurry into a female impression of teeth, thereafter hardening the gypsum slurry, and removing the impression of teeth.

As mentioned above, use of the coloring agent composition according to the present invention makes it possible to produce, through a simple process, a colored gypsum powder and a colored gypsum hardened body which are excellent in colorability and which are uniformly colored without causing the color unevenness. In addition, the gypsum product that can be produced with the coloring agent composition according to the present invention is not limited to gypsum hardened bodies such as a teeth model and an industrial model, and, for example, liquid or semi-liquid gypsum products such as building materials including gypsum plasters and pate, and powdered gypsum products can also be produced.

<Process for Producing Coloring Agent Composition>

Next, the process for producing a coloring agent composition according to the present invention will be described. The method for producing a coloring agent composition according to the present invention includes a first step of mixing a pigment, calcined gypsum, and amorphous silica to obtain a mixed powder. Hereinafter, the details will be described.

(First Step)

In the first step, a pigment, calcined gypsum, and amorphous silica are mixed to obtain a mixed powder. The mixed powder thus obtained can be used as it is as a coloring agent composition. It is preferable that the calcined gypsum used in this case has a volume average particle diameter of 20 to 200 μm, more preferably 20 to 100 μm. Use of the calcined gypsum having a volume average particle diameter within the above-described numerical value range makes it possible to obtain a coloring agent composition capable of producing a gypsum product in which the color unevenness is more difficult to occur and which is more excellent in colorability.

It is preferable that the pigment, the calcined gypsum, and the amorphous silica are separately pulverized in advance to be in a powdered form or a granular form. In order to separately pulverize the pigment, the calcined gypsum, and the amorphous silica, a general pulverizer or the like for pulverizing a powder or a granular product can be used. Specific examples of such a pulverizer include pulverizers (such as a ball mill) that make use of the action of collision or friction using a medium and pulverizers (such as an atomizer) that make use of the action of impact/grinding/shearing. In addition, pulverization can simply be performed by using a juicer-mixer in a table test scale. Moreover, any of batch type pulverizers and one path type pulverizers can be used.

In order to mix the pigment, the calcined gypsum, and the amorphous silica, a general mixer or the like for uniformly mixing a powder can be used. Moreover, the pigment, the calcined gypsum, and the amorphous silica may be mixed by shaking a container or bag in which these components are placed. In addition, specific examples of the mixer include a ribbon mixer, a Nauta mixer, a V type mixer, a paddle mixer, and so on.

In the first step, it is preferable that the pigment, the calcined gypsum, and the amorphous silica are pulverized concurrently with being mixed, namely it is preferable to co-pulverize the pigment, the calcined gypsum, and the amorphous silica. By performing co-pulverization, the calcined gypsum is mixed with the amorphous silica concurrently with being pulverized, making it possible to obtain a coloring agent composition capable of producing a gypsum product in which the color unevenness is more difficult to occur and, furthermore, which is more excellent in colorability as compared with the case where the calcined gypsum and the amorphous silica are simply mixed not through a pulverizer.

In order to co-pulverize the pigment, the calcined gypsum, and the amorphous silica, a general dry pulverizer that is capable of pulverizing a powder concurrently with mixing can be used. Specific examples on the general dry pulverizer include the above-mentioned pulverizers (such as a ball mill) that make use of the action of collision or friction using a medium and pulverizers (such as an atomizer) that make use of the action of impact/grinding/shearing. In addition, co-pulverization can simply be performed by using a juicer-mixer in a table test scale. Moreover, any of batch type pulverizers and one path type pulverizers can be used. The pulverization time is different depending on the amounts of the pigment, the calcined gypsum, and the amorphous silica, the pulverization facilities, and, in the pulverizer using a medium, the material quality, size, weight, and so on of the medium, however the effects due to co-pulverization are exhibited even in an extremely short pulverization time.

The order of supplying the pigment, the calcined gypsum, and the amorphous silica to a pulverizer is different depending on the pulverization system of the pulverizer to be used, but can appropriately be selected. In the case, for example, where a pulverizer is used which completes pulverization in a short time as short as approximately a few seconds, it is preferable to simultaneously supply the pigment, the calcined gypsum, and the amorphous silica. On the other hand, in the case where a pulverizer is used which completes pulverization in a few tens of seconds or more, the pigment, the calcined gypsum and the amorphous silica can be supplied in an arbitrary order.

(Second Step)

It is preferable that the process for producing a coloring agent composition according to the present invention further includes a second step of pulverizing the mixed powder obtained in the above-mentioned first step. By further pulverizing the mixed powder obtained in the first step, the same effects as obtained by the co-pulverization can be obtained. Furthermore, as mentioned above, the calcined gypsum is mixed with the amorphous silica concurrently with being pulverized, making it possible to obtain a coloring agent composition capable of producing a gypsum product in which the color unevenness is more difficult to occur, and, furthermore, which is more excellent in colorability as compared with the case where the calcined gypsum and the amorphous silica are simply mixed not through a pulverizer.

In order to pulverize the mixed powder, a general pulverizer for pulverizing a powder, such as the one used in the first step, can be used, and a juicer-mixer can also be used in a table test in the same manner.

EXAMPLES

Hereinafter, the present invention will be described specifically based on Examples, however the present invention is not limited to these Examples. It is to be noted that "parts" and "%" in Examples and Comparative Examples are based on mass unless otherwise noticed.

(1) Regarding Number Average Particle Diameter of Amorphous Silica

Examples 1-1 to 1-5

In a juicer-mixer (product number "MX-X107", manufactured by Panasonic Corporation), 1 part of a pigment (ultramarine), 30 parts of β hemihydrate gypsum (manufactured by Yoshino Gypsum Co., Ltd., volume average particle diameter: 50 μm) as a base material, and 0.3 parts of amorphous silica having a number average particle diameter shown in Table 1 were placed, and mixed and pulverized for 60 seconds to prepare a coloring agent composition.

In a plastic bag, 100 parts of α hemihydrate gypsum as a raw material powder, 0.1 parts of a hardening adjuster (sodium citrate), and 0.3 parts of the produced coloring agent composition were placed and well shaken for 3 minutes to mix the contents, thereby preparing a colored gypsum powder to evaluate the colorability by the following method. Moreover, to the obtained colored gypsum powder, 24 parts of mixing water was added and mixed, then the resultant slurry was poured into a mold (diameter 50 mm×10 mm) and hardened to prepare a colored gypsum hardened body, and the colorability and color unevenness were evaluated by the following methods.

(Evaluation)

[Colorability]

A color difference meter (product name "Color Meter ZE 2000" manufactured by Nippon Denshoku Industries Co., Ltd.) was used to measure the "−b values" in a CIE LAB (L*a*b*) of the produced colored gypsum powders and colored gypsum hardened bodies, and the measured values were used to evaluate the colorability. The results are shown in Table 1.

[Color Unevenness]

The color unevenness was evaluated by visually observing the produced colored gypsum hardened bodies in accordance with the criteria shown below. The results are shown in Table 1. In addition, when the coloring agent composition aggregates, the aggregated portion is partially colored densely, so that the decision by visual observation becomes easy.

Excellent: the area of the portion where the coloring agent composition aggregates is 5% or less of the whole surface of the colored gypsum hardened body.

Good: the area of the portion where the coloring agent composition aggregates is more than 5% and 20% or less of the whole surface of the colored gypsum hardened body.

Fair: the area of the portion where the coloring agent composition aggregates is more than 20% and 50% or less of the whole surface of the colored gypsum hardened body.

Poor: the area of the portion where the coloring agent composition aggregates is more than 50% of the whole surface of the colored gypsum hardened body.

TABLE 1

| | | Examples | | | | |
|---|---|---|---|---|---|---|
| | | 1-1 | 1-2 | 1-3 | 1-4 | 1-5 |
| Pigment (parts) | | 1 | | | | |
| β Hemihydrate gypsum (parts) | | 30 | | | | |
| Amorphous silica | Blending amount (parts) | 0.3 | | | | |
| | Number average particle diameter (nm) | 5 | 10 | 30 | 40 | 50 |
| Colorability (−b value) | Colored gypsum powder | 15.0 | 14.7 | 14.3 | 14.3 | 13.5 |
| | Colored gypsum hardened body | 28.6 | 28.0 | 27.6 | 27.3 | 27.0 |
| Color unevenness | Colored gypsum hardened body | Excellent | Excellent | Excellent | Good | Fair |

As shown in Table 1, it is understood that the colorability of the colored gypsum powder and colored gypsum hardened body to be obtained is improved and the color unevenness of the colored gypsum hardened body is improved as the number average particle diameter of the amorphous silica is small.

(2) Regarding Blending Amount of Amorphous Silica

Examples 2-1 to 2-6 and Comparative Example 1

In a juicer-mixer (product number "MX-X107", manufactured by Panasonic Corporation), 1 part of a pigment (ultramarine), 30 parts of β hemihydrate gypsum (manufactured by Yoshino Gypsum Co., Ltd., volume average particle diameter: 50 μm) as abase material, and amorphous silica (number average particle diameter: 30 nm) in a blending amount shown in Table 2 were placed, and mixed and pulverized for 60 seconds to prepare a coloring agent composition. Moreover, colored gypsum powders and colored gypsum hardened bodies were prepared and the colorability and color unevenness thereof were evaluated in the same manner as in the case of the aforementioned "Examples 1-1 to 1-5". The results are shown in Table 2.

TABLE 2

| | Comparative Example | Examples | | | | | |
|---|---|---|---|---|---|---|---|
| | 1 | 2-1 | 2-2 | 2-3 | 2-4 | 2-5 | 2-6 |
| Pigment (parts) | 1 | | | | | | |
| β Hemihydrate gypsum (parts) | 30 | | | | | | |

TABLE 2-continued

|  |  | Comparative Example | Examples | | | | | |
|---|---|---|---|---|---|---|---|---|
|  |  | 1 | 2-1 | 2-2 | 2-3 | 2-4 | 2-5 | 2-6 |
| Amorphous silica (parts) |  | 0 | 0.01 | 0.1 | 0.5 | 0.8 | 1 | 1.5 |
| Colorability | Colored gypsum powder | 10.0 | 13.2 | 14.0 | 15.0 | 15.2 | 15.2 | 15.2 |
| (−b value) | Colored gypsum hardened body | 24.6 | 26.5 | 27.9 | 28.1 | 28.6 | 28.4 | 28.1 |
| Color unevenness | Colored gypsum hardened body | Poor | Fair | Good | Excellent | Excellent | Excellent | Excellent |

As shown in Table 2, it is understood that the colorability-improving effect and the color unevenness-improving effect are weak when the content of the amorphous silica is small. In addition, when the content of the amorphous silica is large, the colorability-improving effect and the color unevenness-improving effect are sufficient, however the colored gypsum powder and the colored gypsum hardened body are disadvantageous in terms of costs in some cases.

(3) Regarding Blending Amount of Calcined Gypsum

Examples 3-1 to 3-8 and Comparative Example 2

In a juicer-mixer (product number "MX-X107", manufactured by Panasonic Corporation), 1 part of a pigment (ultramarine), β hemihydrate gypsum (manufactured by Yoshino Gypsum Co., Ltd., volume average particle diameter: 50 μm) as a base material in a blending amount as shown in Table 3, and 0.3 parts of amorphous silica (number average particle diameter: 30 nm) were placed, and mixed and pulverized for 60 seconds to prepare a coloring agent composition. Moreover, colored gypsum powders and colored gypsum hardened bodies were prepared and the colorability and color unevenness thereof were evaluated in the same manner as in the case of the aforementioned "Examples 1-1 to 1-5". The results are shown in Table 3.

As shown in Table 3, it is understood that the colorability-improving effect and the color unevenness-improving effect are weak when the content of β hemihydrate gypsum is small. In addition, it is understood that there is a tendency that the color unevenness is liable to occur when the content of β hemihydrate gypsum is too large.

(4) Regarding Volume Average Particle Diameter of Calcined Gypsum

Examples 4-1 to 4-7

In a juicer-mixer (product number "MX-X107", manufactured by Panasonic Corporation), 1 part of a pigment (ultramarine), 30 parts of β hemihydrate gypsum (manufactured by Yoshino Gypsum Co., Ltd.) as a base material having a volume average particle diameter as shown in Table 4, and 0.3 parts of amorphous silica (number average particle diameter: 30 nm) were placed, and mixed and pulverized for 60 seconds to prepare a coloring agent composition. Moreover, colored gypsum powders and colored gypsum hardened bodies were prepared and the colorability and color unevenness thereof were evaluated in the same manner as in the case of the aforementioned "Examples 1-1 to 1-5". The results are shown in Table 4.

TABLE 3

|  |  | Comparative Example | Examples | | | | | | | |
|---|---|---|---|---|---|---|---|---|---|---|
|  |  | 2 | 3-1 | 3-2 | 3-3 | 3-4 | 3-5 | 3-6 | 3-7 | 3-8 |
| Pigment (parts) |  |  |  |  |  | 1 |  |  |  |  |
| Amorphous silica (parts) |  |  |  |  |  | 0.3 |  |  |  |  |
| β Hemihydrate gypsum (parts) |  | 0 | 0.5 | 1 | 10 | 30 | 50 | 80 | 100 | 130 |
| Colorability | Colored gyspum powder | 10.3 | 12.9 | 14.3 | 15.6 | 15.5 | 15.6 | 15.0 | 14.3 | 14.3 |
| (−b value) | Colored gypsum hardened body | 25.7 | 26.0 | 26.4 | 27.5 | 27.5 | 27.5 | 27.0 | 26.8 | 26.8 |
| Color unevenness | Colored gypsum hardened body | Poor | Fair | Excellent | Excellent | Excellent | Excellent | Excellent | Excellent | Good |

TABLE 4

|  |  | Examples | | | | | | |
|---|---|---|---|---|---|---|---|---|
|  |  | 4-1 | 4-2 | 4-3 | 4-4 | 4-5 | 4-6 | 4-7 |
| Pigment (parts) |  |  |  |  | 1 |  |  |  |
| Amorphous silica (parts) |  |  |  |  | 0.3 |  |  |  |
| β Hemihydrate gypsum | Blending amount (parts) |  |  |  | 30 |  |  |  |
|  | Volume average particle diameter (μm) | 10 | 20 | 50 | 100 | 150 | 200 | 250 |

TABLE 4-continued

|  |  | Examples | | | | | | |
| --- | --- | --- | --- | --- | --- | --- | --- | --- |
|  |  | 4-1 | 4-2 | 4-3 | 4-4 | 4-5 | 4-6 | 4-7 |
| Colorability | Colored gypsum powder | 13.3 | 14.0 | 15.0 | 15.0 | 14.3 | 13.9 | 13.4 |
| (−b value) | Colored gypsum hardened body | 26.8 | 26.5 | 28.6 | 28.4 | 28.4 | 26.8 | 27.0 |
| Color unevenness | Colored gypsum hardened body | Fair | Excellent | Excellent | Excellent | Good | Good | Fair |

As shown in Table 4, it is understood that there is a tendency that the color unevenness is liable to occur when the volume average particle diameter of β hemihydrate gypsum is too small or too large.

(5) Regarding Kind of Base Material (Calcined Gypsum)

Examples 5-1 to 5-3 and Comparative Examples 3 to 5

In a juicer-mixer (product number "MX-X107", manufactured by Panasonic Corporation), 1 part of a pigment (ultramarine), 30 parts of the kind of base material as shown in Table 5, and 0.3 parts of amorphous silica (number average particle diameter: 30 nm) were placed, and mixed and pulverized for 60 seconds to prepare a coloring agent composition. In addition, any of α hemihydrate gypsum, β hemihydrate gypsum, and type III anhydrous gypsum used was manufactured (volume average particle diameter: 50 μm) by Yoshino Gypsum Co., Ltd. Moreover, colored gypsum powders and colored gypsum hardened bodies were prepared and the colorability and color unevenness thereof were evaluated in the same manner as in the case of the aforementioned "Examples 1-1 to 1-5". The results are shown in Table 5.

(6) Regarding Mixing Method

Examples 6-1 and 6-2

In a juicer-mixer (product number "MX-X107", manufactured by Panasonic Corporation), 1 part of a pigment (ultramarine), 30 parts of the kind of base material as shown in Table 6, and 0.3 parts of amorphous silica (number average particle diameter: 30 nm) were placed, and mixed and pulverized for 60 seconds to prepare a coloring agent composition. Moreover, colored gypsum powders and colored gypsum hardened bodies were prepared and the colorability and color unevenness thereof were evaluated in the same manner as in the case of the aforementioned "Examples 1-1 to 1-5". The results are shown in Table 6.

Examples 6-3 and 6-4

In a plastic bag, 1 part of a pigment (ultramarine), 30 parts of the kind of base material as shown in Table 6, and 0.3 parts of amorphous silica (number average particle diameter: 30 nm) were placed and well shaken for 60 seconds to mix the contents, thereby preparing a coloring agent composition. Moreover, colored gypsum powders and colored gypsum hardened bodies were prepared and the colorability and color unevenness thereof were evaluated in the same manner as in the case of the aforementioned "Examples 1-1 to 1-5". The results are shown in Table 6.

TABLE 5

|  |  | Examples | | | Comparative Examples | | |
| --- | --- | --- | --- | --- | --- | --- | --- |
|  |  | 5-1 | 5-2 | 5-3 | 3 | 4 | 5 |
| Pigment (parts) |  | | | 1 | | | |
| Amorphous silica (parts) |  | | | 0.3 | | | |
| Base material | Bldending amount (parts) | | | 30 | | | |
|  | Kind | β Hemihydrate gypsum | α Hemihydrate gypsum | Type III anhydrous gypsum | Calcium carbonate | Silica | Talc |
| Colorability | Colored gypsum powder | 15.0 | 14.7 | 14.3 | 12.2 | 12.7 | 13.4 |
| (−b value) | Colored gypsum hardened body | 28.6 | 28.4 | 26.8 | 26.5 | 27.3 | 25.2 |
| Color unevenness | Colored gypsum hardened body | Excellent | Excellent | Good | Fair | Poor | Poor |

As shown in Table 5, it is understood that the colorability-improving effect and the color unevenness-improving effect are obtained by using α hemihydrate gypsum, β hemihydrate gypsum, and type III anhydrous gypsum, which are each calcined gypsum, as a base material. In addition, it is understood that a more excellent colorability-improving effect and a more excellent color unevenness-improving effect are obtained in the case where α hemihydrate gypsum or β hemihydrate gypsum is used as compared with the case where type III anhydrous gypsum is used.

Comparative Examples 6 and 7

In a plastic bag, 1 part of a pigment (ultramarine) and 30 parts of the kind of base material as shown in Table 6 were placed and well shaken for 60 seconds to mix the contents, thereby preparing a coloring agent composition. Moreover, colored gypsum powders and colored gypsum hardened bodies were prepared and the colorability and color unevenness thereof were evaluated in the same manner as in the case of the aforementioned "Examples 1-1 to 1-5". The results are shown in Table 6.

TABLE 6

|  |  | Examples | | | | Comparative Examples | |
| --- | --- | --- | --- | --- | --- | --- | --- |
|  |  | 6-1 | 6-2 | 6-3 | 6-4 | 6 | 7 |
| Pigment (parts) | | 1 | | | | | |
| Amorphous silica (parts) | | 0.3 | | 30 | | 0 | 0 |
| Base material | Blending amount (parts) | | | | | | |
| | Kind | α Hemihydrate gypsum | β Hemihydrate gypsum | α Hemihydrate gypsum | β Hemihydrate gypsum | α Hemihydrate gypsum | β Hemihydrate gypsum |
| First step | | *1 | | *2 | | *2 | |
| Colorability | Colored gypsum powder | 14.7 | 15.0 | 9.2 | 10.0 | 6.2 | 7.1 |
| (−b value) | Colored gypsum hardened body | 28.4 | 28.6 | 27.3 | 24.6 | 23.0 | 23.6 |
| Color unevenness | Colored gypsum hardened body | Excellent | Excellent | Fair | Good | Poor | Poor |

*1: Juicer-Mixer was used (pulverization was performed concurrently with mixing).
*2: Plastic bag was used (mixing alone).

As shown in Table 6, it is understood that the colorability-improving effect and the color unevenness-improving effect are more improved by not only simply mixing but also pulverizing the pigment, the base material (calcined gypsum), and the amorphous silica concurrently with mixing (namely, by performing co-pulverization).

(7) Regarding Kind of Gypsum (Matter to be Colored)

Examples 7-1 to 7-5 and 8-1 to 8-5

In a juicer-mixer (product number "MX-X107", manufactured by Panasonic Corporation), 1 part of a pigment (ultramarine), 30 parts of the kind of base material (manufactured by Yoshino Gypsum Co., Ltd., volume average particle diameter: 50 μm) as shown in Tables 7 and 8, and 0.3 parts of amorphous silica (number average particle diameter: 30 nm) were placed, and mixed and pulverized for 60 seconds to prepare a coloring agent composition. Moreover, colored gypsum powders and colored gypsum hardened bodies were prepared and the colorability and color unevenness thereof were evaluated in the same manner as in the case of the aforementioned "Examples 1-1 to 1-5" except that the kinds of gypsum (matter to be colored) as shown in Tables 7 and 8 were used as a raw material powder gypsum (matter to be colored). The results are shown in Tables 7 and 8. However, in the case where dihydrate gypsum or type II anhydrous gypsum was used as gypsum (matter to be colored), the colored gypsum hardened body was not prepared and the evaluation of color unevenness was not conducted. In addition, both the dihydrate gypsum and the type II anhydrous gypsum used were manufactured by Yoshino Gypsum Co., Ltd.

TABLE 7

|  |  | Examples | | | | |
| --- | --- | --- | --- | --- | --- | --- |
|  |  | 7-1 | 7-2 | 7-3 | 7-4 | 7-5 |
| Pigment (parts) | | 1 | | | | |
| Amorphous silica (parts) | | 0.3 | | | | |
| Base material | Blending amount (parts) | 30 | | | | |
| | Kind | α Hemihydrate gypsum | | | | |
| Gypsum (matter to be colored) | | Dihydrate gypsum | α Hemihydrate gypsum | β Hemihydrate gypsum | Type II anhyrous gypsum | Type III anhydrous gypsmn |
| Colorability | Colored gypsum powder | 14.3 | 14.7 | 14.9 | 14.4 | 14.7 |
| (−b value) | Colored gypsum hardened body | — | 28.4 | 28.4 | — | 27.3 |
| Color unevenness | Colored gypsum hardened body | — | Excellent | Excellent | — | Excellent |

TABLE 8

|  |  | Examples | | | | |
| --- | --- | --- | --- | --- | --- | --- |
|  |  | 8-1 | 8-2 | 8-3 | 8-4 | 8-5 |
| Pigment (parts) | | 1 | | | | |
| Amorphous silica (parts) | | 0.3 | | | | |
| Base material | Blending amount (parts) | 30 | | | | |
| | Kind | α Hemihydrate gypsum | | | | |
| Gypsum (matter to be colored) | | Dihydrate gypsum | α Hemihydrate gypsum | β Hemihydrate gypsum | Type II anhyrous gypsum | Type III anhydrous gypsmn |
| Colorability | Colored gypsum powder | 14.6 | 15.0 | 15.0 | 14.7 | 14.7 |
| (−b value) | Colored gypsum hardened body | — | 28.6 | 28.4 | — | 27.6 |

TABLE 8-continued

|  |  | Examples | | | | |
| --- | --- | --- | --- | --- | --- | --- |
|  |  | 8-1 | 8-2 | 8-3 | 8-4 | 8-5 |
| Color unevenness | Colored gypsum hardened body | — | Excellent | Excellent | — | Excellent |

As shown in Tables 7 and 8, it is understood that an excellent colorability-improving effect and an excellent color unevenness-improving effect are obtained in the case where any kind of gypsum was used as the matter to be colored.

INDUSTRIAL APPLICABILITY

Use of the coloring agent composition according to the present invention makes it possible to produce, without causing color unevenness, a gypsum hardened body such as a teeth model and an industrial model; and a liquid, semi-liquid, or powdered gypsum product which are uniformly colored.

The invention claimed is:

1. A coloring agent composition to be added to a gypsum-containing raw material powder forming a gypsum product and to be used for coloring the gypsum product, the coloring agent composition consisting essentially of:
   a pigment;
   calcined gypsum; and
   amorphous silica,
   wherein the amorphous silica has a number average particle diameter in a range from 5 to 40 nm,
   the calcined gypsum is a hemihydrate gypsum, β hemi-hydrate gypsum, or a mixture thereof, and
   the coloring agent composition is in a powder form.

2. The coloring agent composition according to claim 1, wherein a content of the amorphous silica is in a range from 0.01 to 1 part by mass relative to 1 part by mass of the pigment.

3. The coloring agent composition according to claim 1, wherein a content of the calcined gypsum is in a range from 1 to 100 parts by mass relative to 1 part by mass of the pigment.

4. The coloring agent composition according to claim 1, wherein the amorphous silica has a number average particle diameter in a range from 5 to 30 nm.

5. The coloring agent composition according to claim 1, wherein the pigment, the calcined gypsum, and the amorphous silica have been co-pulverized.

6. A process for producing the coloring agent composition according to claim 1, the process comprising:
   a first step of mixing the pigment, the calcined gypsum, and the amorphous silica so as to form a mixed powder.

7. The process for producing the coloring agent composition according to claim 6,
   wherein the pigment, the calcined gypsum, and the amorphous silica are pulverized concurrently with the mixing in the first step.

8. The process for producing the coloring agent composition according to claim 6,
   further comprising a second step of pulverizing the mixed powder.

9. The process for producing the coloring agent composition according to claim 6,
   wherein the calcined gypsum has a volume average particle diameter in a range from 20 to 200 μm.

10. A colored gypsum powder composition for forming the gypsum product comprising:
    the coloring agent composition according to claim 1; and
    the gypsum-containing raw material powder.

11. A process for producing a colored gypsum powder composition, comprising:
    adding the coloring agent composition according to claim 1 to the gypsum-containing raw material powder.

12. A process for producing a gypsum product, comprising:
    adding the coloring agent composition according to claim 1 to the gypsum-containing raw material powder so as to form a colored gypsum power composition;
    forming a slurry of the colored gypsum power composition; and
    forming the gypsum product from the slurry.

* * * * *